(12) United States Patent
van Rens (10) Patent No.: US 11,877,895 B2
(45) Date of Patent: Jan. 23, 2024

(54) CMUT DEVICE AND IMAGING METHOD (71) Applicant: KONINKLIJKE PHILIPS N.V., Eindhoven (NL)

(72) Inventor: Antonia Cornelia van Rens, Nuenen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1021 days.

(21) Appl. No.: 16/464,346

(22) PCT Filed: Nov. 22, 2017

(86) PCT No.: PCT/EP2017/079986
§ 371 (c)(1),
(2) Date: May 28, 2019

(87) PCT Pub. No.: WO2018/095937
PCT Pub. Date: May 31, 2018

(65) Prior Publication Data
US 2021/0113195 A1    Apr. 22, 2021

(30) Foreign Application Priority Data

Nov. 28, 2016 (EP) ..................... 16200864

(51) Int. Cl.
*A61B 8/00* (2006.01)
*A61B 8/14* (2006.01)
*B06B 1/02* (2006.01)

(52) U.S. Cl.
CPC ................. *A61B 8/54* (2013.01); *A61B 8/14* (2013.01); *A61B 8/4494* (2013.01); *B06B 1/0215* (2013.01); *B06B 1/0292* (2013.01); *B06B 2201/51* (2013.01); *B06B 2201/76* (2013.01)

(58) Field of Classification Search
None
See application file for complete search history.

(56) References Cited

U.S. PATENT DOCUMENTS

| 8,847,648 | B2 | 9/2014 | Barroso et al. | |
|---|---|---|---|---|
| 2006/0004289 | A1 | 1/2006 | Tian et al. | |
| 2006/0084875 | A1* | 4/2006 | Knight | A61B 8/12 600/462 |
| 2007/0167814 | A1* | 7/2007 | Wakabayashi | A61B 8/445 600/459 |

(Continued)

FOREIGN PATENT DOCUMENTS

JP    S5827426 A    2/1983

OTHER PUBLICATIONS

International Search Report and Written Opinion for International Application No. PCT/EP2017/079986, filed Nov. 22, 2017, 18 pages.

(Continued)

*Primary Examiner* — Katherine L Fernandez (57) ABSTRACT

A capacitive micro-machined ultrasonic transducer (CMUT) device in which integrated probe circuitry includes both the ultrasound transmission and reception circuitry and a DC-DC converter for generating a bias voltage for the CMUT cell. The high voltage pulses of a pulser circuit and a high voltage DC bias voltage are both generated by a single probe circuit, which is local to the CMUT cell.

12 Claims, 4 Drawing Sheets

(56) References Cited

U.S. PATENT DOCUMENTS

| | | | |
|---|---|---|---|
| 2013/0079642 A1* | 3/2013 | Marshall | A61B 8/12 |
| | | | 600/463 |
| 2014/0327378 A1 | 11/2014 | Van Rens | |
| 2014/0360272 A1* | 12/2014 | Kandori | B06B 1/0207 |
| | | | 310/300 |
| 2015/0018678 A1 | 1/2015 | Komuro | |
| 2015/0087991 A1 | 3/2015 | Chen et al. | |
| 2016/0310992 A1* | 10/2016 | Van Rens | B06B 1/0292 |
| 2018/0015504 A1* | 1/2018 | Zhao | B06B 1/0207 |
| 2018/0248477 A1* | 8/2018 | Kline | H02M 1/08 |

OTHER PUBLICATIONS

Villar-Pique, et al., "survey and benchmark of fully integrate switching power converters: switched-capacitor versus inductive approach", IEEE transactions on power electronics, vol. 28, Issue 9, Sep. 2013. (Abstract).

Breussegem, et al., "A DMOS integrated 320 mW capacitive 12V to 70V DC/DC converter for LIDAR applications", 2009 IEEE Energy Conversion Congress and Exposition, Sep. 19, 2009, vol. 1, pp. 1-5.

Meyvaert, et al., "monolithic switched-capacitor DC-DC towards high voltage conversion ratios", 2014 IEEE 15th Workshop on Control and Modeling for Power Electronics (COMPEL), Date of Conference Jun. 22-25, 2014. (Abstract).

* cited by examiner

CMUT DEVICE AND IMAGING METHOD

RELATED APPLICATION

This application is the U.S. National Phase application under 35 U.S.C. § 371 of International Application No. PCT/EP2017/079986, filed on Nov. 22, 2017, which claims the benefit of European Application No. EP16200864.3, filed Nov. 28, 2016. These applications are hereby incorporated by reference herein.

FIELD OF THE INVENTION

This invention relates to capacitive micromachined ultrasonic transducer (CMUT) devices.

BACKGROUND OF THE INVENTION

Ultrasound is widely used for medical diagnostic scans. To be able to do electronic beam-forming in 2D or 3D, the transducers are being produced in large arrays with transducer element sizes of $\lambda/2$ where $\lambda$ is the wavelength of the used ultrasound frequency in body tissue.

Because of the small feature size possible with micromachining technology, CMUT devices can be produced for high-frequency beam-forming arrays. Moreover, it is possible integrate the CMUT array monolithically with the driving and sensing electronics which makes CMUTs suited for miniaturized and low-cost ultrasound applications.

As a complicating factor, CMUTs require a high bias voltage (e.g. 50-120V) to operate. During transmit, the high-voltage (HV) transmit pulse is added to the bias voltage. The overall transducer voltage may be up to 200V which is not compatible with most area- and cost-efficient application specific integrated circuit (ASIC) technologies. To be able to work with compact high voltage ASIC technologies, the CMUT bias voltage is typically separated from the ASIC driving and receiving electronics. The bias is for example generated in the ultrasound imaging system or in the probe system connector. The bias is transferred to the transducer array via a wire running through the system cable. Locally at the transducer array, a HV decoupling capacitor is used to close the current loop for high frequencies. The capacitor typically is rather large as it has to withstand high voltages and the required impedance at the operating frequency has to be low (e.g. <1Ω). The product of electrical capacitance and voltage reflects the stored charge, which is restricted by safety regulations.

The need for the extra wire and decoupling capacitor increases the cost and required area of a CMUT array transducer head. This is a problem for low cost and miniaturized systems. The bias voltage wire may also complicate safety regulation approval.

There is therefore a need for a system configuration which addresses these issues to provide a cost-effective miniaturized solution to the requirement for a high bias voltage for CMUT devices.

US 2006/0004289 discloses a CMUT device having a pulser circuit and a bias voltage bank which uses DC-DC converters.

US 2015/0018678 discloses a bias generating apparatus for an ultrasound system a having a transmission pulser circuit in an observation apparatus and a DC-DC converter in a power supply circuit in a separate connector part.

SUMMARY OF THE INVENTION

The invention is defined by the claims.

According to examples in accordance with an aspect of the invention, there is provided a capacitive micro-machined ultrasound transducer, CMUT, device comprising:
  a CMUT cell; and
  probe circuitry physically and electrically connected to the CMUT cell, wherein the probe circuitry comprises:
    ultrasound transmission circuitry including a pulser circuit;
    ultrasound reception circuitry; and
    a DC-DC converter for generating a bias voltage for the CMUT cell.
  wherein the pulser circuit and the DC-DC converter are integrated as a single probe circuit.

In this device, the high voltage pulses of a pulser circuit and a high voltage DC bias voltage are both generated by a single probe circuit, which is typically an application specific integrated circuit (ASIC) which is located within the ultrasound probe, i.e. at the probe location. The pulser circuit and the DC-DC converter are in particular formed as a single integrated circuit.

The CMUT cell and the probe circuitry are physically connected, by which is meant they are joined to form, or integrated into, a single circuit device, and this is located at the probe, i.e. at a probe head. This avoids the need to feed a high voltage CMUT DC bias to the probe.

The CMUT cell is preferably monolithically integrated with the probe circuitry. Thus, the CMUT cell, pulser circuit and DC-DC converter are monolithically integrated, together with other circuit components of the ultrasound transmission and reception circuitry.

The DC-DC converter for example comprises a capacitive switch mode converter. This can be integrated with the other probe circuitry as part of a single high voltage-ASIC. All voltages that need to be generated in the probe circuitry should remain within the voltage compliance range of the circuitry, e.g. ASIC.

For this purpose, the CMUT cell may for example comprise:
  a substrate;
  a cell membrane opposing the substrate with a gap between;
  a first electrode coupled to the cell membrane;
  a second electrode embedded into a cell floor opposing the first electrode and separated therefrom by a gas or vacuum cavity; and
  a third electrode which is capacitively coupled with the first or second electrode, wherein the bias voltage is provided to the third electrode.

This monolithically integrated three-electrode design (and therefore three-terminal cell) limits the high-voltage requirements of the probe circuitry (e.g. ASIC). In particular, the high voltage DC bias is applied to the third terminal, so that the two voltage components (the pulser circuit voltage and the bias voltage) are on separate terminals, so that the probe circuitry does not need to operate at the sum of those voltages. The DC-bias voltage is connected to the middle of three electrodes.

This 3-terminal device also enables the size of a high-voltage decoupling capacitor close to the transducer array to be reduced. This is achieved because the main AC-current flow no longer runs via the CMUT decoupling capacitor but directly from the pulser output to ground.

The capacitive coupling is for example realized by a dielectric layer sandwiched between and being in direct contact with the capacitively coupled electrodes. The third electrode is for example located in the cell floor.

The ultrasound transmission circuitry and the ultrasound reception circuitry are coupled to the first electrode and the second electrode for causing and sensing vibration of the membrane. Thus, there are different terminals for the bias voltage as for the ultrasound generation and sensing signals.

There may be no storage capacitor for the bias voltage external to the probe circuitry. This enables further miniaturization.

An ultrasonic probe may comprise an array of CMUT devices as defined above. The array may be used for 2D or 3D ultrasound imaging.

The invention also provides an ultrasonic imaging system comprising the ultrasonic probe as defined above, and a controller for controlling the ultrasound transmission circuitry, ultrasound reception circuitry and DC-DC converter.

The controller may be adapted to provide (i) ultrasound signal generation and processing and (ii) DC-DC conversion, in a time sequential manner. This prevents degradation of the ultrasound image caused by the disturbances resulting from the DC-DC converter operation.

Examples in accordance with another aspect of the invention provide an ultrasound imaging method, comprising:
using a probe circuitry which is physically and electrically connected to a CMUT cell to:
generate ultrasound transmission pulses;
detect ultrasound echo signals; and
generate a bias voltage for the CMUT cell using a DC-DC converter of the probe circuitry,
wherein the method comprises generating ultrasound transmission pulses and generating a bias voltage for the CMUT cell using a single integrated probe circuit.

This method provides local generation of the bias voltage as well as the ultrasound transmission pulses.

The method may comprise providing the bias voltage to a third electrode of a three-electrode CMUT cell, having a first electrode coupled to a cell membrane, a second electrode embedded into a cell floor opposing the first electrode and separated therefrom by a gas or vacuum cavity and a third electrode which is capacitively coupled with the first or second electrode. The third electrode, to which the DC-bias voltage is applied, is for example the middle of the three electrodes, between the first and second electrodes.

The method may then comprise controlling the probe circuitry to provide (i) ultrasound signal generation and processing and (ii) DC-DC conversion, in a time sequential manner. Operating in a time sequential manner is made possible because the DC-DC conversion has to provide only a low current which means that the output voltage of the DC-DC converter is not likely to drop, even when there is only a small output storage capacitor for the bias voltage.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a capacitive micro-machined ultrasonic transducer, CMUT, device in which integrated probe circuitry includes both the ultrasound transmission and reception circuitry and a DC-DC converter for generating a bias voltage for the CMUT cell. The high voltage pulses of a pulser circuit and a high voltage DC bias voltage are both generated by a single probe circuit (ASIC), which is local to the CMUT cell.

Figure 1:
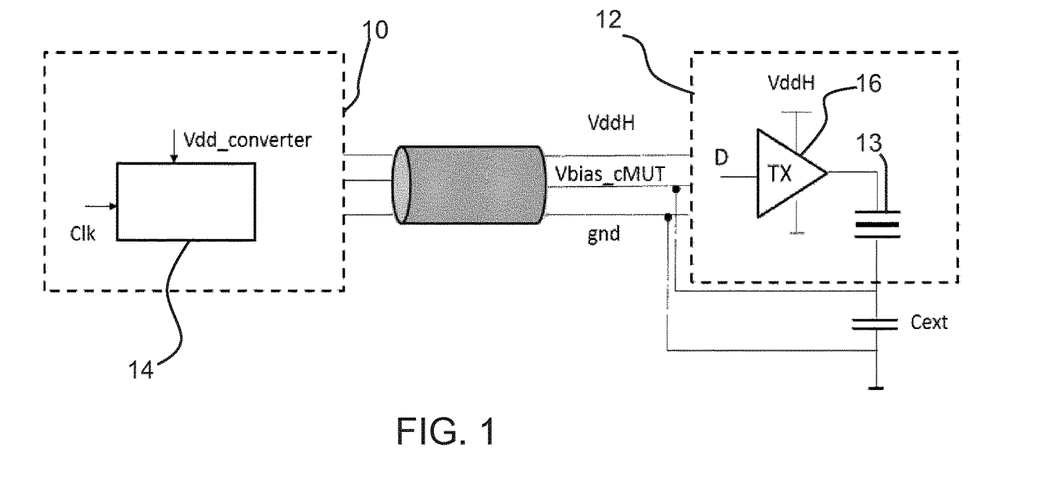
FIG. 1 shows a typical system configuration for a CMUT device.

FIG. 1 shows a typical system configuration for a CMUT device.

The system comprises a main system part 10 and a probe part comprising an ASIC 12 which includes the transducer array. One transducer cell 13 is shown in FIG. 1. The system part 10 provides control signals (not shown in FIG. 1) and supply voltages (partly shown in FIG. 1) to the probe part and receives returned echo signals and performs the analysis of the echo signals.

The main system part 10 includes a DC-DC converter 14 for generating the required CMUT bias voltage (Vbias_cMUT) and it also provides a supply voltage VddH to the probe part (ASIC) 12. The required transmit pulse is generated locally at the probe using a transmit amplifier or transmission gate which is part of the ASIC and is powered by the supply voltage VddH.

The bias voltage is stored on an external capacitor Cext (i.e. external to the ASIC of the transducer array), whereas the high voltage driving and low-voltage receiving electronics (supplied by yet another supply voltage VddL which is not shown in FIG. 1) is provided on the ASIC of the probe part. For simplicity, only a single transmit amplifier (voltage driver) 16 is shown, to represent the transmit circuitry. Receive circuitry will also be present, supplied the supply VddL.

Figure 2:
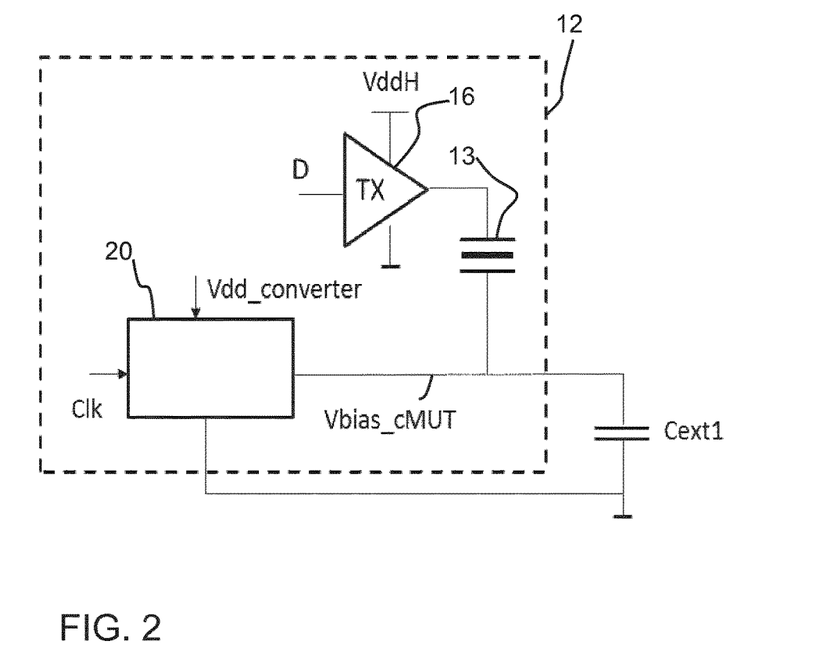
FIG. 2 shows an example of the probe part in accordance with an aspect of the invention.

FIG. 2 shows an example of the probe part in accordance with an aspect of the invention.

The ASIC 12 of the probe part again comprises the transmit and receive circuitry (again, only the transmit amplifier 16 is shown). In addition, there is a local DC-DC converter 20 for generating the CMUT bias voltage Vbias_cMUT. The DC-DC converter 20 can be supplied by VddH or VddL. In the example shown in FIG. 2, the bias voltage is again stored on an external capacitor Cext1. However, as will be discussed further below, further measures may be adopted to reduce the size of the external capacitor or else avoid the need for external storage altogether.

The DC-DC converter 20 comprises a switch mode circuit. Such circuits comprise an energy storing element or arrangement, such as an inductor and/or capacitor arrangement, and a switching arrangement for providing energy transfer to and from the energy storage element or arrangement. The circuits enable voltage up-conversion or down-conversion and voltage inversion.

A preferred implementation of switch mode DC-DC converter is a switched-capacitor converter, as this is more easily integrated into the ASIC compared to an inductive converter. As the CMUT elements do not dissipate energy from the bias-voltage node, the power efficiency of the DC-DC converter is not critical.

The DC-DC converter 20, e.g. switched capacitor converter, is monolithically integrated with the ultrasound driver and sense ASIC 12.

There are issues which may be resolved in order to facilitate integration of the DC-DC converter 20 into the ASIC 12, and the way these issues are addressed is explained below.

A first issue is that the high-voltage requirements of the ASIC may rise, as the ASIC components are exposed to the sum of the CMUT bias voltage and the high voltage pulser supply voltage (VddH).

The output of the voltage driver 16 varies between VddH and ground. The external capacitor Cext1 closes the current loop (the current flows from VddH via the output of the voltage driver 16, the transducer cell 13 and the capacitor Cext back to ground.

A second issue is that because of the switching behavior of the DC-DC converter, the imaging performance of the transducer may be compromised.

To address the first issue, and to avoid increased high-voltage ASIC technology requirements, a particular type of CMUT probe may be used. This is a three-terminal CMUT as described in WO2015/086413. This design enables the maximum voltage seen by the ASIC components to be limited to the maximum out of the CMUT bias voltage and the pulser supply voltage (VddH).

For example, this means that the I4T70 ASIC technology of ON semiconductor (trade mark) can generate an ASIC CMUT bias voltage of 70V and have a pulser integrated running on a supply of 50V. When using a normal CMUT design, a 120V compliant ASIC technology would be needed.

The three-terminal CMUT technology will now be discussed briefly, and reference is made to WO2015/086413 for further details.

The three-terminal design is based on a capacitive micromachined ultrasonic transducer cell having a third electrode, whereby a first or second electrode is capacitively coupled with the third electrode. The capacitive coupling is realized by a dielectric layer sandwiched between and being in direct contact with the capacitively coupled electrodes.

This design of the CMUT cell, comprising three electrodes integrated into the cell, means the ultrasound transducer and a capacitive component are implemented within one CMUT cell. The capacitive component is for example used to form one part of an RC-filter (known as a bias T-filter) for separating an AC component of the received signal from the DC component so that the ASIC for processing the detection signals only processes the AC component and is not exposed to the high (DC bias) voltages.

The separate third electrode is located between the two main electrodes and has capacitive coupling to each of two main electrodes of the CMUT cell, wherein the two electrodes are separated by the CMUT cavity. In particular, the third electrode is capacitively coupled to one of the two electrodes via the CMUT cavity and to another electrode through the dielectric layer, wherein the latter relation defines a capacitor for integration into the CMUT cell RC filter.

Figure 3:
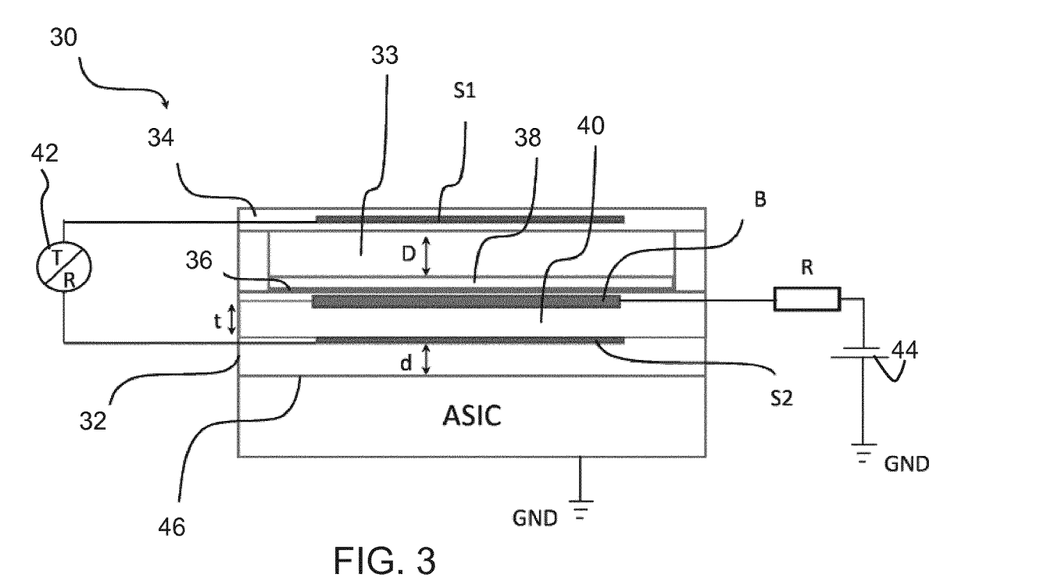
FIG. 3 shows an example of a three-terminal CMUT cell which may be used in the probe part of FIG. 2.

FIG. 3 shows an embodiment of the three-terminal CMUT cell 30 of WO 2015/086413.

A flexible membrane or diaphragm 34 is suspended above (or opposing) a substrate 32 with a cavity (gap) 33 there between. The substrate can be made of either silicon or another CMOS compatible material such as glass. A first electrode S1 is coupled to the cell membrane 34 and can move with the membrane 34. A third (bottom) electrode B is embedded into the cell floor 36 of the cell comprising an upper surface of the substrate 32. Other realizations of the electrode S1 design can be considered, such as electrode S1 may be embedded in the membrane 34 or it may be deposited on the membrane 34 as an additional layer. In this example, the third electrode B is circularly configured and embedded into the cell floor 36.

In addition, the membrane 34 is fixed relative to the top face of the substrate 32 and configured and dimensioned so as to define a spherical or cylindrical cavity 33 between the membrane 34 and the substrate 32.

The cell and its cavity 33 may have alternative geometries. For example, cavity 33 could define a rectangular or square cross-section, a hexagonal cross-section, an elliptical cross-section, or an irregular cross-section.

The third electrode B is typically insulated on its cavity-facing surface with an additional insulating layer 38. A preferred insulating layer is a silicon dioxide (Si02) dielectric layer deposited in a tetra ethyl oxysilane (TEOS) based PECVD process, formed above the third electrode B and below the first electrode S1. An alternative material for the insulating layer 38 can be high-k dielectrics and oxides (aluminum oxide, various grades including silane, SiH4, based PECVD Si02).

High-k dielectrics and oxides can be also deposited using atomic layer deposition (ALD) technique. The insulating layer may advantageously reduce charge accumulation which leads to device instability and drift and reduction in acoustic output pressure. Use of the insulating layer is desirable with CMUTs with collapsed membrane, which will be described with reference to FIG. 4. This type of CMUT is more susceptible to charge retention than CMUTs operated with suspended membranes.

The components may be fabricated from CMOS compatible materials, e.g., Al, Ti, nitrides (e.g., silicon nitride), oxides (various grades: thermal or TEOS/SiH4 LPCVD/PECVD based), poly-silicon and the like. In a CMOS fabrication, for example, the oxide and nitride layers may be formed by chemical vapor deposition and the metallization (electrode) layer put down by a sputtering process. Suitable CMOS processes are LPCVD and PECVD, the latter having a relatively low operating temperature of less than 400° C.

Exemplary techniques for producing the cavity 33 involve defining the cavity in an initial portion of the membrane 34 before adding a top face of the membrane 34. In FIG. 3, the diameter of the cavity 33 may be larger than the diameter of the third electrode B. First electrode S1 may have the same outer diameter as the third electrode B, although such conformance is not required. Thus, in an example the first electrode S1 is fixed relative to the top face of the membrane 34 so as to align with the third electrode B below.

The CMUT fabrication process can comprise a sacrificial release process, wherein the cavity underneath of the membrane is formed by first applying a sacrificial layer on the substrate, then applying the membrane layer followed by the removing of the sacrificial layer with a selective etchant. Alternatively, a wafer bonding process may be used, wherein the cavity is formed on the prime wafer and the membrane in another wafer, then both wafers are bonded together such that the cavity confined by the membrane is formed.

A second electrode S2 of the CMUT cell is deposited onto the substrate 32 opposing the third electrode B on the side opposite to the cavity 33. Thus, the third electrode B is located in between the first electrode S1 and the second electrode S2. A dielectric layer with a thickness "t" is in direct contact and sandwiched between the second and the third electrodes S2 and B; thus, providing a capacitive relation between these two electrodes.

The first electrode S1 and the third electrode B of the CMUT cell 30 provide the capacitive plates of the CMUT device and a gap of the cavity 33 having a thickness "D" in combination with the additional insulating layer 38 form the dielectric between the plates of the capacitor.

The first electrode S1 can be brought in vibration by means of a signal transmitter/receiver 42 adapted to apply an AC voltage over the second electrode S2 and the first electrode S1, which result in the generation of an acoustic beam. When subsequently the membrane vibrates as a result of the received acoustic signal, the changing dimension of the dielectric gap between the electrodes leads to changing capacitance of the CMUT which is detected by the signal transmitter/receiver 42, coupled to the first and second electrodes S1 and S2, as the response of the CMUT cell 30 to a received acoustic echo.

CMUT device sensitivity can improved by increasing electric field through the cavity 33, which may be achieved following ways: (i) reduced effective dielectric thickness of the CMUT, defined by the spacing and dielectric constant of the dielectric between the first and third electrodes and (ii) increased amount of "free" charge collected on the electrodes. The effective dielectric thickness is reduced in the collapsed mode, which is achieved by applying sufficient DC voltage; and the amount of the collected charge can be increased with increasing the DC bias voltage. The spacing between the CMUT electrodes (S1 and B) is controlled by applying the DC bias voltage to the third electrode B from a DC bias source 44. This bias source is in the examples in accordance with the invention formed as a DC-DC converter which is part of the ASIC beneath the CMUT cell. Thus, the bias source is shown as an external component only for the sake of clarity of the drawing.

For transmission, the first electrode S1 and the second electrode S2 are driven (controlled) by an RF generator (generalized as the signal transmitter/receiver 42) whose AC signal causes the membrane to vibrate and transmit an acoustic signal. This transmitter/receiver 42 is in the examples in accordance with the invention also formed as part of the ASIC beneath the CMUT cell. Thus, the transmit and receive circuitry is shown as an external component only for the sake of clarity of the drawing.

The substrate 32 of the CMUT cell 30 can be coupled to a top surface 46 of the application specific circuitry (ASIC) layer, wherein the distance between the second electrode S2 and the top surface 46 of the ASIC layer is denoted as "d". Commonly the distance "d" can be defined by a buried oxide layer (not shown in the figure), that has an insulating function for the second electrode S2 towards the ASIC electronics. The buried oxide layer can be a silicon oxide layer (optionally in combination with a silicon nitride layer) with the thickness of around 2 micrometers.

The CMUT cell 30 can be either manufactured on top of the ASIC in a sequence of CMOS processes or attached to the ASIC through a flip-chip technique, for example. In either case, the CMUT cell is physically and electrically connected to the ASIC in such a way as to form a single entity which is local to the transducer probe, and hence remote from the main system control side.

Figure 4:
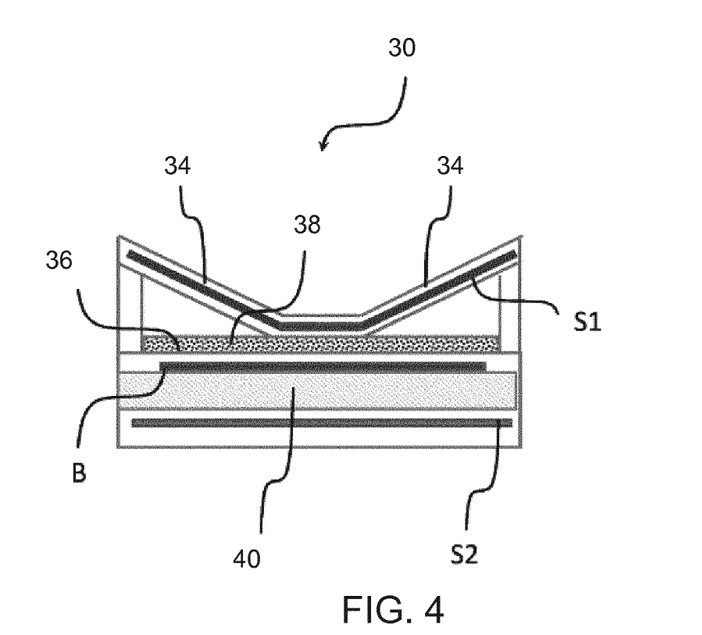
FIG. 4 shows an example of the CMUT cell operation, wherein the membrane of the CMUT cell is a collapsed membrane.

FIG. 4 shows an example of the CMUT cell operation, wherein the membrane 34 of the CMUT cell 30 is a collapsed membrane. The collapsed membrane 34 during the CMUT cell operation may be made collapsed relative to the cell floor and the suspended portions of the membrane 34 can be adapted to move/vibrate under an applied electrical signal between electrodes. From a technology point of view, the CMUT cell 30 with a collapsed membrane can in principle be manufactured in any conventional way, comprising steps of providing a CMUT with a membrane and applying different means, such as electrical (bias voltage), mechanical, membrane stress or pressure, in order to bring the membrane to a collapsed state.

In the collapsed mode the CMUT capacitance is determined mainly by the additional insulating layer 38 and applied voltage. For example, a circular CMUT device having diameter of 60 micrometers may have 500 nm thick additional insulating layer 38. The CMUT capacitance is around 0.04 pF at zero applied DC voltage and around 0.1 pF (2.5 times higher) in the collapsed mode at 140V DC bias voltage. For other CMUT geometries, this ratio may vary.

The implementation of second electrode S2 in the substrate of the CMUT cell permits separation of an AC signal component from the DC bias voltage commonly applied to the CMUT device. This reduces the dimensions of the CMUT related electronics in the ultrasound probe, in case both signal electrodes (membrane and substrate) are actively controlled.

One of the ways to arrange the CMUT devices in an array is providing a network of RC filters to the CMUT array, wherein a DC bias voltage is applied to each CMUT device through the RC filter. In this arrangement, the CMUT array will comprise a discrete high-voltage coupling capacitor and a discrete high impedance resistor for each interconnected CMUT device. The dimensions of the discrete RC filter components may be disadvantageous for scaling down an ultrasound probe comprising the CMUT array.

The three-electrode CMUT cell provides a CMUT device with an integrated capacitive part of the RC filter (the resistive part typically will be realized in the ASIC).

Figure 5:
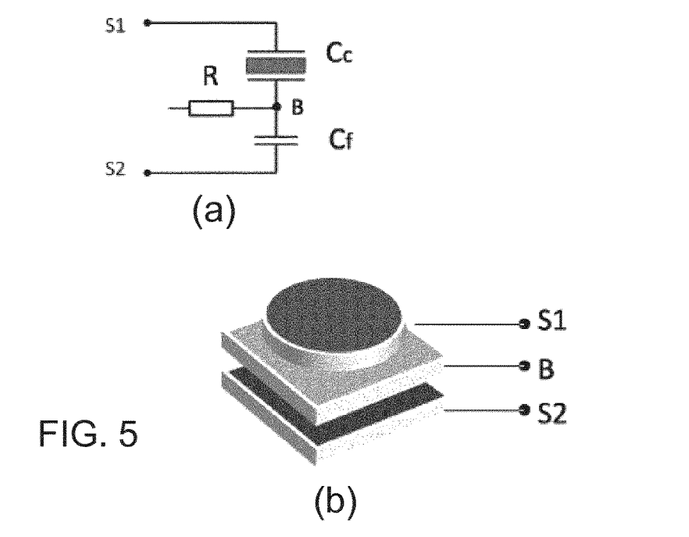
FIG. 5 shows an electrical equivalent circuit model of the three-electrode CMUT cell.

The effective circuit is shown in FIG. 5.

The third electrode B is used to provide a DC bias voltage to the CMUT cell, while the capacitive part of the integrated RC filter is realized through the conductive plates of the third electrode B and the second electrode S2 separated by the dielectric layer 40.

Referring to FIG. 5(a) in order to provide an efficient RC-filtering the capacitive relation Cf between the third and second electrodes B anf S2 is equal to or larger than the CMUT device capacitance Cc between the first and third electrodes S1 and B. This condition results from the fact that for high frequencies, the series connection of Cc and Cf causes an attenuation of the signal according to (Cc+Cf)/Cf, the higher Cf is the lower signal is attenuated. The signal attenuation happens during both transmission and reception and may be limited by increasing Cf.

In case of a fixed value of Cc, the condition of Cf>Cc can be realized by tuning the thickness "t" of the dielectric layer 40 and/or a dielectric constant of the material of the layer. The value of the capacitance Cf of the integrated RC-filter can be further improved by increasing overlap areas of the third and second electrodes B and S2 in relation to the first electrodes. An example of this is illustrated in FIG. 5(b).

The circular shaped first electrode S1 has smaller diameter than the dimensions of the third and second electrodes B and S2, both having equal square shape. Note the typical Cc value scales with the number of the CMUT cells in the array.

The dielectric layer 40 can be made of commonly known insulating materials, such as silicon dioxide, nitrides (e.g., silicon nitride) or high-k dielectrics. In a CMOS fabrication, for example, the oxide and nitride layers may be formed by chemical vapor deposition. Suitable CMOS processes are also LPCVD and PECVD, the latter having a relatively low operating temperature of less than 400° C.

Using the three-terminal CMUT design outlined above meant the main transducer current does not flow via the external decoupling capacitor (Cext1), so that the required decoupling capacitor can be much smaller (by a factor of 10-100) and it may be possible to fully rely on an on-chip decoupling capacitor. Note that using a reduced capacitor value also is beneficial from a safety regulation point of view.

Figure 6:
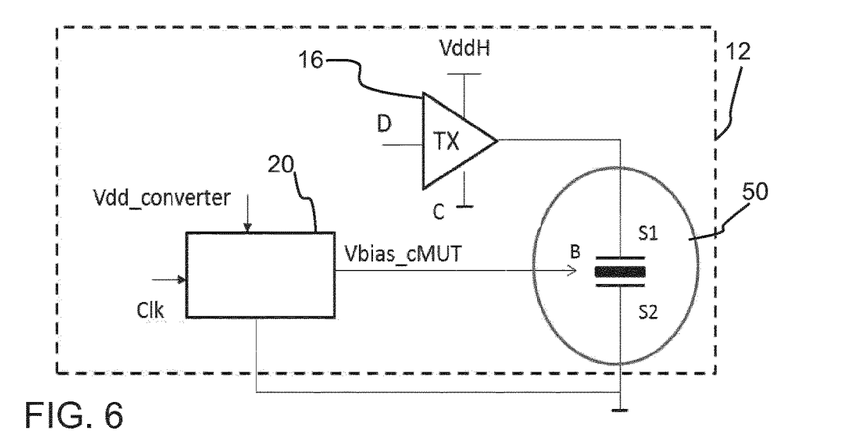
FIG. 6 shows an implementation of the circuit of FIG. 2 using the three-terminal CMUT device.

FIG. 6 shows an implementation of the circuit of FIG. 2 using the three-terminal CMUT device 50, in which the bias voltage Vbias_cMUT is applied to the third terminal B, and also in which no external capacitor is used.

To address the second issue, of compromised imaging performance, a customized control scheme may be used, that switches the DC-DC converter when the ultrasound imaging is turned off, while it turns off the clock of the DC-DC converter when ultrasound imaging is active.

Alternating activation is feasible because the CMUT devices do not dissipate energy (other than by leakage) from the third terminal due to the capacitive (rather than galvanic) coupling to the remainder of the CMUT structure.

This means the power efficiency of the DC-DC converter is not critical, and it also means that alternating activation of the DC-DC converter and the CMUT array imaging function is feasible.

Figure 7:
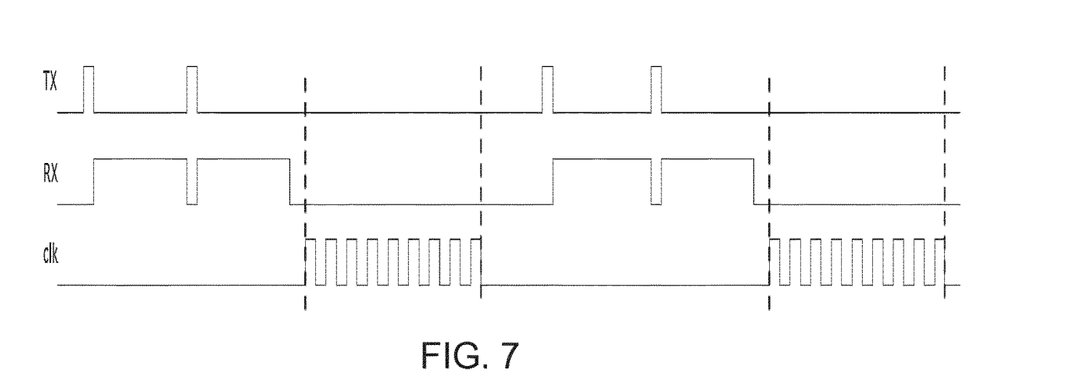
FIG. 7 shows an example of timing scheme for an ultrasound imaging method.

FIG. 7 shows an example of timing scheme for the alternated operation.

The ultrasound data acquisition involves generation of transmit events (shown by plot TX) and receiving acoustic echo signals (shown by plot RX).

The ultrasound data acquisition (TX and RX) is alternated with operation of the DC-DC converter, as represented by the clock signal "clk" used for operating the switch mode DC-DC converter.

The DC-DC converter implemented within the probe ASIC does not need to be highly efficient. In particular, implementing a highly efficient DC-DC converter will typically require a large number of discrete components, hence a large area, as well as appropriate filtering to suppress switching noise.

The voltage generated by the DC-DC converter in the device described above is for biasing the CMUT. The CMUT bias does not deliver any current or suffer significant dissipation. The voltage is instead only for pre-charging the CMUT device to give the CMUT sensitivity to receive echo signals and to improve linearity of the device in the transmit mode. As the bias node does not have to deliver real energy, the power efficiency of the DC-DC converter is not important. This opens up the solution of turning off the DC-DC charge pump circuit during the ultrasound imaging, as explained above, as well as enabling monolithic integration without large external energy storage and filtering components.

The invention is of particular interest for miniaturized and low-cost solutions, for example for use in a probe unit suitable for interventional applications wherein space requirements are very strict. These interventional applications for example include intravascular ultrasound (IVUS), flow sensing based on Doppler ultrasound, and intercardiac echocardiography (ICE), for example forward looking ICE (FL-ICE).

Figure 8:
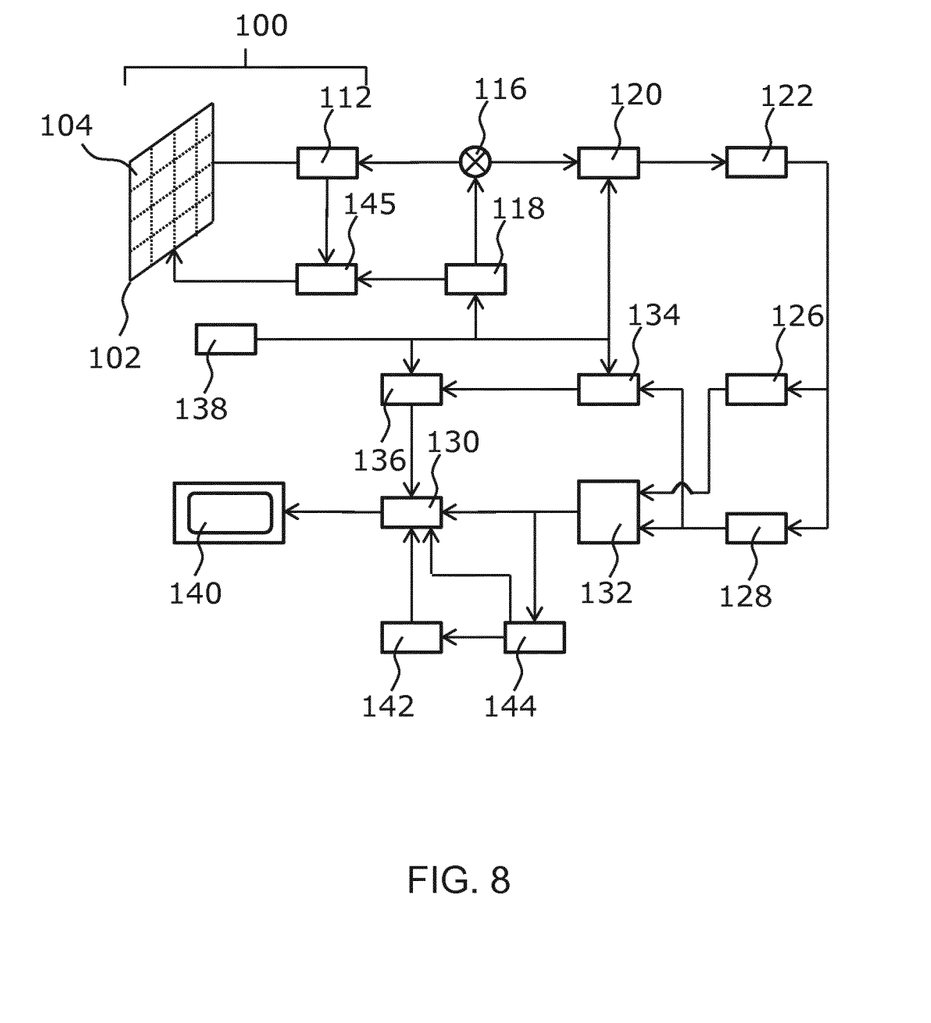
FIG. 8 shows one possible system architecture for an ultrasound imaging system.

For completeness, one example of the general operation of an ultrasound diagnostic imaging system will now be described, with reference to FIG. 8.

The system comprises an array transducer probe 100 which has a CMUT transducer array 102 for transmitting ultrasound waves and receiving echo information. The transducer array 102 may alternatively comprise piezoelectric transducers formed of materials such as PZT or PVDF. The transducer array 102 is a two-dimensional array of transducers 104 capable of scanning in a 2D plane or in three dimensions for 3D imaging.

The transducer array 102 is coupled to a microbeamformer 112 in the probe which controls reception of signals by the CMUT array cells or piezoelectric elements. Microbeamformers are capable of at least partial beamforming of the signals received by sub-arrays (or "groups" or "patches") of transducers as described in U.S. Pat. No. 5,997,479 (Savord et al.), U.S. Pat. No. 6,013,032 (Savord), and U.S. Pat. No. 6,623,432 (Powers et al.).

Note that the microbeamformer is entirely optional. The examples below assume no analog beamforming.

The microbeamformer 112 is coupled by the probe cable to a transmit/receive (T/R) switch 116 which switches between transmission and reception and protects the main beamformer 120 from high energy transmit signals when a microbeamformer is not used and the transducer array is operated directly by the main system beamformer. The transmission of ultrasound beams from the transducer array 102 is directed by a transducer controller 118 coupled to the microbeamformer by the T/R switch 116 and a main transmission beamformer (not shown), which receives input from the user's operation of the user interface or control panel 138.

One of the functions controlled by the transducer controller 118 is the direction in which beams are steered and focused. Beams may be steered straight ahead from (orthogonal to) the transducer array, or at different angles for a wider field of view. The transducer controller 118 can be coupled to control a DC bias control 145 for the CMUT array. The DC bias control 145 sets DC bias voltage(s) that are applied to the CMUT cells.

In the reception channel, partially beamformed signals are produced by the microbeamformer 112 and are coupled to a main receive beamformer 120 where the partially beamformed signals from individual patches of transducers are combined into a fully beamformed signal. For example, the main beamformer 120 may have 128 channels, each of which receives a partially beamformed signal from a patch of dozens or hundreds of CMUT transducer cells or piezoelectric elements. In this way the signals received by thousands of transducers of a transducer array can contribute efficiently to a single beamformed signal.

The beamformed reception signals are coupled to a signal processor 122. The signal processor 122 can process the received echo signals in various ways, such as band-pass filtering, decimation, I and Q component separation, and harmonic signal separation which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting the noise at higher frequencies from greater depths where these frequencies are devoid of anatomical information.

The beamformers for transmission and for reception are implemented in different hardware and can have different functions. Of course, the receiver beamformer is designed taking into account the characteristics of the transmission beamformer. In FIG. 8 only the receiver beamformers 112, 120 are shown, for simplicity. In the complete system, there will also be a transmission chain with a transmission micro beamformer, and a main transmission beamformer.

The function of the microbeamformer 112 is to provide an initial combination of signals in order to decrease the number of analog signal paths. This is typically performed in the analog domain.

The final beamforming is done in the main beamformer 120 and is typically after digitization.

The transmission and reception channels use the same transducer array 102 which has a fixed frequency band. However, the bandwidth that the transmission pulses occupy can vary depending on the transmission beamforming that has been used. The reception channel can capture the whole transducer bandwidth (which is the classic approach) or by using bandpass processing it can extract only the bandwidth that contains the useful information (e.g. the harmonics of the main harmonic).

The processed signals are coupled to a B mode (i.e. brightness mode, or 2D imaging mode) processor 126 and a Doppler processor 128. The B mode processor 126 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 128 processes temporally distinct signals from tissue movement and blood flow for the detection of the motion of substances such as the flow of blood cells in the image field. The Doppler processor 128 typically includes a wall filter with parameters which may be set to pass and/or reject echoes returned from selected types of materials in the body.

The structural and motion signals produced by the B mode and Doppler processors are coupled to a scan converter 132 and a multi-planar reformatter 144. The scan converter 132 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field with their Doppler-estimated velocities to produce a color Doppler image which depicts the motion of tissue and blood flow in the image field. The multi-planar reformatter will convert echoes which are received from points in a common plane in a volumetric region of the body into an ultrasound image of that plane, as described in U.S. Pat. No. 6,443,896 (Detmer). A volume renderer 142 converts the echo signals of a 3D data set into a projected 3D image as viewed from a given reference point as described in U.S. Pat. No. 6,530,885 (Entrekin et al.).

The 2D or 3D images are coupled from the scan converter 132, multi-planar reformatter 144, and volume renderer 142 to an image processor 130 for further enhancement, buffering and temporary storage for display on an image display 140. In addition to being used for imaging, the blood flow values produced by the Doppler processor 128 and tissue structure information produced by the B mode processor 126 are coupled to a quantification processor 134. The quantification processor produces measures of different flow conditions such as the volume rate of blood flow as well as structural measurements such as the sizes of organs and gestational age. The quantification processor may receive input from the user control panel 138, such as the point in the anatomy of an image where a measurement is to be made. Output data from the quantification processor is coupled to a graphics processor 136 for the reproduction of measurement graphics and values with the image on the display 140, and for audio output from the display 140. The graphics processor 136 can also generate graphic overlays for display with the ultrasound images. These graphic overlays can contain standard identifying information such as patient name, date and time of the image, imaging parameters, and the like. For these purposes the graphics processor receives input from the user control panel 138, such as patient name. The user interface is also coupled to the transmit controller 118 to control the generation of ultrasound signals from the transducer array 102 and hence the images produced by the transducer array and the ultrasound system. The transmit control function of the controller 118 is only one of the functions performed. The controller 118 also takes account of the mode of operation (given by the user) and the corresponding required transmitter configuration and band-pass configuration in the receiver analog to digital converter. The controller 118 can be a state machine with fixed states.

The user interface is also coupled to the multi-planar reformatter 144 for selection and control of the planes of multiple multi-planar reformatted (MPR) images which may be used to perform quantified measures in the image field of the MPR images.

Other overall system architectures are of course possible. This invention does not require any alteration to the standard known signal processing and scanning functions.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An ultrasound imaging caste comprising:
   a controller; and
   a capacitive micro-machined ultrasound transducer (CMUT) device, wherein the CMUT device comprises:
      a CMUT cell comprising a first electrode, a second electrode, and a third electrode, wherein the third electrode is capacitively coupled with the first electrode; and
      probe circuitry physically and electrically connected to the CMUT cell, wherein the probe circuitry comprises:
         ultrasound transmission circuitry including a pulser circuit configured to apply AC voltage over the first and second electrodes of the CMUT cell for transmitting acoustic signals;

ultrasound reception circuitry configured to receive acoustic echo signals responsive to the acoustic signals for performing ultrasound data acquisition; and a switch mode DC-DC converter configured to generate and apply a high bias voltage to the third electrode of the CMUT cell, wherein the pulser circuit and the switch mode DC-DC converter are integrated as a single probe circuit, wherein the controller is configured to control operation of the ultrasound transmission circuitry and the ultrasound reception circuitry to perform the ultrasound data acquisition, and to control the switch mode DC-DC converter to generate the high bias voltage alternately with the operation of the ultrasound transmission circuitry and the ultrasound reception circuitry for performing the ultrasound data acquisition.

2. The system as claimed in claim 1, wherein the probe circuitry is an application specific integrated circuit (ASIC), wherein at least the pulser circuit and the switch mode DC-DC converter are monolithically integrated in the ASIC.

3. The system as claimed in claim 2, wherein the second electrode is disposed on a substrate, which is coupled to a top surface of the ASIC.

4. The system as claimed in claim 1, wherein the CMUT cell is monolithically integrated with the probe circuitry.

5. The system claimed in claim 1, wherein the switch mode DC-DC converter comprises a capacitive switch mode converter.

6. The system as claimed in claim 1, wherein the capacitive coupling is realized by a dielectric layer sandwiched between and being in direct contact with the capacitively coupled first and third electrodes.

7. The system as claimed in claim 6, wherein the ultrasound transmission circuitry and the ultrasound reception circuitry are coupled to the first electrode and the second electrode for causing and sensing vibration of a membrane coupled to the first electrode.

8. The system as claimed in claim 6, wherein there is no storage capacitor for the high bias voltage external to the probe circuitry.

9. The system as claimed in claim 1, wherein the third electrode is located in a cell floor of the CMUT cell.

10. The system as claimed in claim 1, further comprising an ultrasonic probe comprising an array of CMUT devices according to claim 1.

11. The system as claimed in claim 1, wherein the controller is adapted to provide (i) ultrasound signal generation and processing and (ii) DC-DC conversion, in a time sequential manner.

12. The system as claimed in claim 1, wherein the high bias voltage generated by the switch mode DC-DC converter is in a range of about 50V to about 120V.

* * * * *